United States Patent [19]

Tjoeng et al.

[11] Patent Number: 5,272,162
[45] Date of Patent: Dec. 21, 1993

[54] PLATELET AGGREGATION INHIBITORS

[75] Inventors: Foe S. Tjoeng, Manchester, Mo.; Jeffery A. Zablocki, Skokie, Ill.

[73] Assignee: G. D. Searle & Co., Chicago, Ill.

[21] Appl. No.: 908,128

[22] Filed: Jul. 2, 1992

[51] Int. Cl.$^5$ .................. C07C 229/00; A01N 43/40
[52] U.S. Cl. ........................ 514/344; 514/344; 514/345; 514/346; 514/347; 514/512; 514/522; 514/542; 514/564; 546/332; 546/286; 546/14; 546/300; 546/294; 560/34; 562/439; 558/270
[58] Field of Search .............. 562/439; 560/34; 546/231, 233, 290, 297, 298, 300, 302, 303, 332, 286, 14, 294; 514/529, 331, 512, 542, 344, 345, 346, 347, 564, 522; 558/270

[56] References Cited

U.S. PATENT DOCUMENTS

| | | | |
|---|---|---|---|
| 4,570,006 | 2/1986 | Fujii et al. | 560/34 |
| 4,673,582 | 6/1987 | Nofre et al. | 562/439 |
| 5,030,653 | 7/1991 | Trivedi | 562/439 |
| 5,086,069 | 2/1992 | Klein et al. | 562/439 |

FOREIGN PATENT DOCUMENTS

| | | |
|---|---|---|
| 90101404.3 | 1/1990 | European Pat. Off. |
| 91103462.7 | 3/1991 | European Pat. Off. |

*Primary Examiner*—José G. Dees
*Assistant Examiner*—Keith MacMillan
*Attorney, Agent, or Firm*—Cynthis S. Kovacevic; Roger A. Williams

[57] ABSTRACT

This invention relates to compounds having the following formula

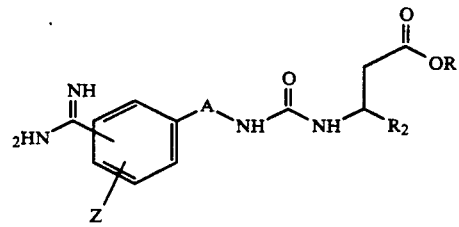

or a pharmaceutically acceptable salt thereof which are useful in the inhibition of platelet aggregation, to pharmaceutical compositions including the compounds and to a method of inhibiting platelet aggregation in mammals by administering such compounds and compositions.

30 Claims, No Drawings

PLATELET AGGREGATION INHIBITORS

FIELD OF THE INVENTION

The present invention relates to pharmaceutical agents and compounds which inhibit platelet aggregation in mammals.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

European Patent Application 445,796 discloses platelet aggregation inhibitors which contain peptide linkages, namely N-[N-[4-(p-amidinobenzamido)butyryl]-L-α-aspartyl]valine compounds. The compounds inhibit cell-cell adhesion and the binding of adhesive proteins to platelets.

European Patent Application 372,486 discloses N-acyl beta amino acid derivatives which are useful as cell adhesion inhibitors and are especially useful for inhibiting platelet aggregation.

European Patent Application 381,033 discloses amidino or guanidinoaryl substituted alkanoic acid derivatives which inhibit protein to receptor binding and are useful for the treatment of thrombosis and cardiac infarction.

SUMMARY OF THE INVENTION

The present invention relates to a class of compounds represented by the formula:

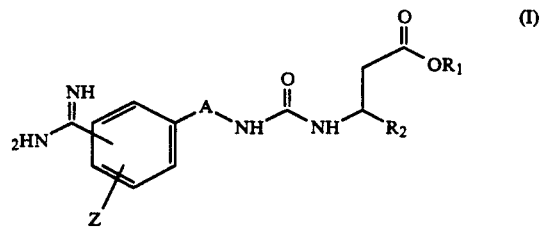

or a pharmaceutically acceptable salt thereof wherein Z is selected from the group consisting of H, halogen, hydroxy, alkoxy of one to six carbon atoms and alkyl of one to six carbon atoms;

wherein A is selected from the group consisting of alkyl of one to six carbon atoms, alkenyl of two to six carbon atoms and alkynyl of two to six carbon atoms;

wherein $R_1$ is selected from the group consisting of H, alkyl of one to six carbon atoms, aralkyl and alkanoyloxyalkyl; and wherein $R_2$ is selected from the group consisting of H, alkyl of one to six carbon atoms, alkenyl of two to six carbon atoms, alkynyl of two to six carbon atoms, aryl and heteroaryl wherein the heteroatom is N all optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

It is another object of the invention to provide pharmaceutical compositions comprising compounds of the formula I. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

The present invention relates to a class of compounds represented by the formula I, described above.

A preferred embodiment of the present invention is a compound of the formula I wherein:

Z is hydrogen;

A is alkyl of one to six carbon atoms; wherein $R_1$ is selected from the group consisting of H and alkyl of one to six carbon atoms; and $R_2$ is selected from the group consisting of hydrogen, alkyl of one to six carbon atoms, alkenyl of two to six carbon atoms and alkynyl of two to six carbon atoms all optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

Another preferred embodiment of the present invention is a compound of the formula I wherein:

Z is hydrogen;

A is alkyl of one to six carbon atoms;

$R_1$ is selected from the group consisting of hydrogen and alkyl of one to six carbon atoms; and R₂ is aryl optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

Still another preferred embodiment is a compound of the formula I wherein:

Z is hydrogen;
A is alkyl of one to six carbon atoms;
$R_1$ is selected from the group consisting of hydrogen and alkyl of one to six carbon atoms; and
$R_2$ is a heteroaryl wherein the heteroatom is N, optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

Exemplifying these embodiments are the following compounds:

ethyl β-[[[[4-[4-(aminoiminomethyl)phenyl]-butyl]amino]carbonyl]amino]-3-pyridinepropanoate β-[[[[4-[4-(aminoiminomethyl)phenyl]butyl]amino]carbonyl]amino]-3-pyridinepropanoic acid ethyl β-[[[[4-[4-(aminoiminomethyl)phenyl]butyl]amino]carbonyl]amino]benzenepropanoate β-[[[[4-[4-(aminoiminomethyl)phenyl]butyl]amino]carbonyl]amino]benzenepropanoic acid 3-[[[[4-[4-(aminoiminomethyl)phenyl]butyl]amino]carbonyl]amino]butanoic acid ethyl 3-[[[4-[4-(aminoiminomethyl)phenyl]butyl]amino]carbonyl]amino]propanoat ethyl 3-[[[[4-[4-(aminoiminomethyl)phenyl]butyl]amino]carbonyl]amino]-5-hexenoate ethyl 3S-[[[[4-[4-(aminoiminomethyl)phenyl]butyl]amino]carbonyl]amino]-4-pentenoate 3S-[[[[4-[4-(aminoiminomethyl)phenyl]butyl]amino]carbonyl]amino]-4-pentenoic acid ethyl 3S-[[[[4-[4-(aminoiminomethyl)phenyl]butyl]amino]carbonyl]amino]-4-pentynoate 3-[[[[4-[4-(aminoiminomethyl)phenyl]butyl]amino]carbonyl]amino]propanoic acid, monohydrochloride.

As used herein, the term "alkyl" refers to a straight chain or branched chain hydrocarbon radical having from 1 to 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein, the term "alkoxy" includes straight or branched chain lower alkyl ether radicals wherein the term alkyl is as defined above. Examples of such groups are methoxy, ethoxy, n-propoxy, n-butoxy, isobutoxy, t-butoxy, sec-butoxy, isopropoxy and the like.

As used herein the term "halogen" refers to chloro (Cl), fluoro (F), bromo (Br) or iodo (I).

As used herein the term "alkenyl" refers to unsaturated acyclic hydrocarbons containing at least one double bond and 2 to 6 carbon atoms. Examples of such groups are ethenyl, propenyl, butenyl, isobutenyl, pentenyl, hexenyl and the like.

As used herein the term "alkynyl" refers to acyclic hydrocarbons containing one or more triple bonds and 2 to 6 carbon atoms. Examples of such groups are ethynyl, propynyl, butynyl, pentynyl, hexynyl and the like.

As used herein, the term "lower alkylene" refers to a straight chain or branched chain divalent hydrocarbon radical having from 1 to 6 carbon atoms. Examples of such alkylene radicals are methylene, ethylene, n-propylene, isoproylene, n-butylene, isobutylene, sec-butylene, t-butylene, pentylene, neopentylene, hexylene, isohexylene and the like.

As used herein the term "lower alkenylene" refers to unsaturated acyclic bivalent hydrocarbons containing at least one double bond and 2 to 6 carbon atoms. Examples of such groups are ethenylene, propneylene, buenylene, isobutenylene, pentenylene, hexenylene and the like.

As used herein the term "alkynylene" refers to acyclic bivalent hydrocarbons containing one or more triple bonds and 2 to 6 carbon atoms. Examples of such groups are ethynylene, propynylene, butynylene, pentynylene, hexnylene and the like.

As used herein the term "heteroaryl wherein the heteroatom is N" refers to a radical composed of at least one unsaturated ring wherein one of the carbon atoms is replaced by nitrogen. Examples of such groups are pyridyl, quinolinyl, and the like.

As used herein the term "aralkyl" refers to a radical wherein an aryl group, such as phenyl, naphthyl or pyridyl is attached to an alkyl radical as defined above. Examples of such radicals include benzyl, phenylpropyl, pyridylmethyl and the like.

As used herein the term "aryl" refers to an organic radical derived from an aromatic hydrocarbon by the removal of one atom such as phenyl from benzene and the like.

As used herein the term "carboxyl derivatives" refer to a radical of the general formula

wherein R is hydrogen or alkyl as defined above.

As used herein the term ∫alkoxycarbonyl" refer to a radical of the formula

wherein R is an alkyl group as defined above.

As used herein "alkylamino" refers to a radical of the formula —NHR or —NRR wherein R is an alkyl group as defined above.

The compounds herein as shown in Formula I can exist in various isomeric forms and all such isomeric forms are intended to be included as well as pharmaceutically acceptable salts of such compounds and isomers.

In the structures and formulas herein, a bond drawn across a bond of a ring can be to any available atom on the ring.

The term "pharmaceutically acceptable salt" refer to a salt prepared by conventional means. Examples of pharmaceutically acceptable salts include the hydrochloride, hydrobromide, hydroiodide, sulfate, phosphate, acetate, propionate, lactate, maleate, malate, succinate, and tartrate salts. (See Berge et. al., *J. Pharm. Sci.*, 66(I), 1–19 (1977) for additional examples of pharmaceutically acceptable salts.)

This invention also relates to a method of inhibiting platelet aggregation and more specifically, a method of treatment involving the administration of compounds of Formula I to achieve such inhibition.

The platelet aggregation inhibitors of the present invention are useful in the prevention of re-occlusion of an artery following re-canalization procedures such as post-fibrinolytic therapy, thrombolytic therapy, angioplasty and coronary bypass surgery. Other contemplated uses are prevention of recurrent myocardial infarct, unstable angina, peripheral artery disease, cerebral ischemia and shunt procedures.

For the inhibition of platelet aggregation, compounds of the present invention may be administered orally, parenterally, or by inhalation spray, rectally, or topically in dosage unit formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 150 mg per kilogram of body weight per day are useful in the treatment of the above-indicated conditions.

The pharmacologically active compounds of this invention can be processed in accordance with conventional methods of galenic pharmacy to produce medicinal agents for administration to patients, e.g., mammals including humans.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about I to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

General synthetic sequences for preparing the compounds of formula I are outlined in Schemes A-G.

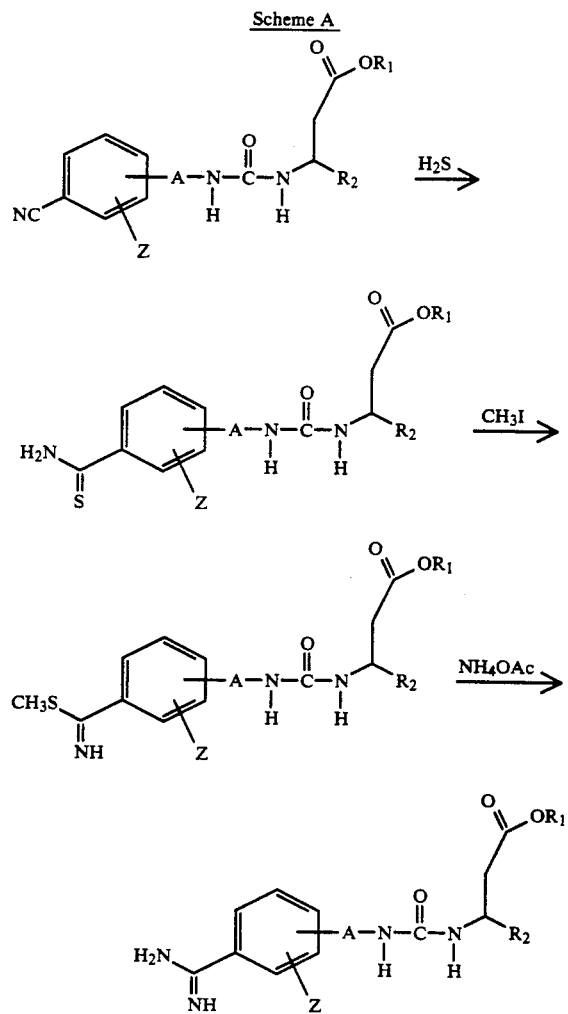

Scheme B
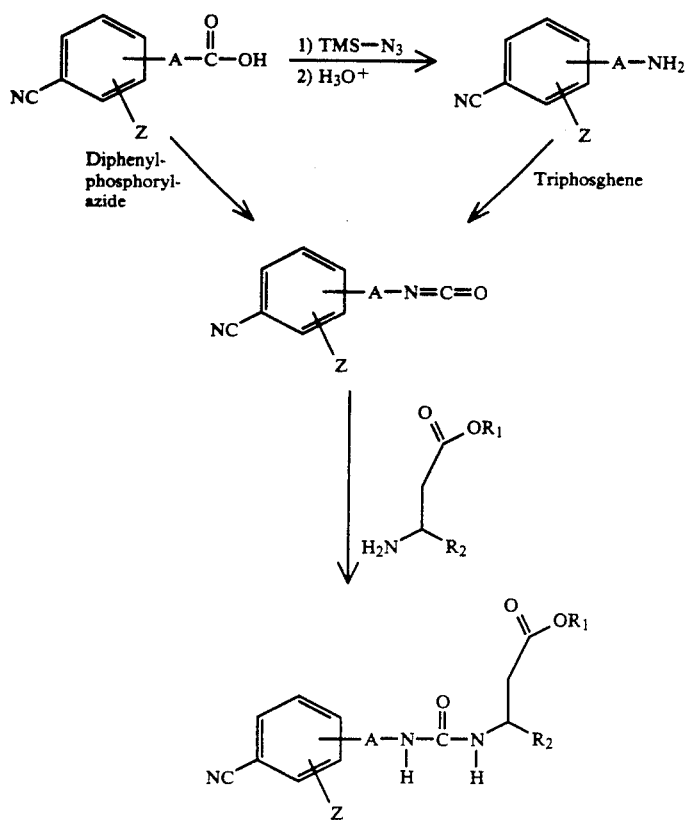
SCHEME C
Method 1
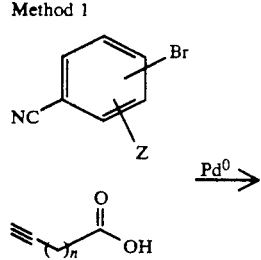
Method 2
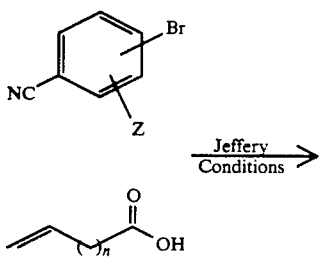
-continued
SCHEME C
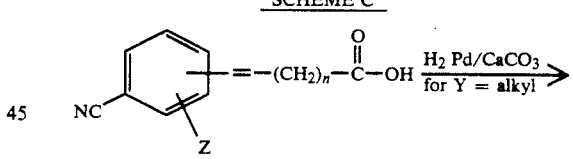
Method 3
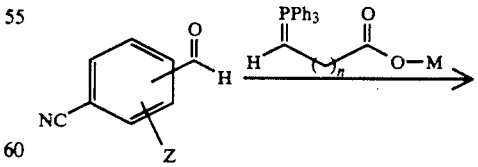
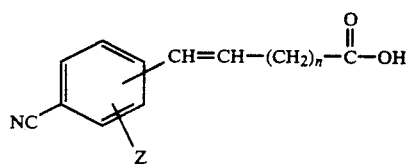

Scheme D
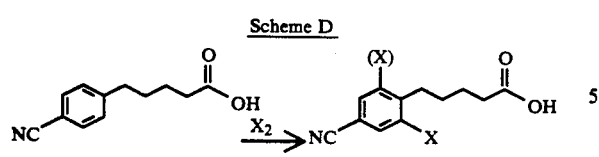
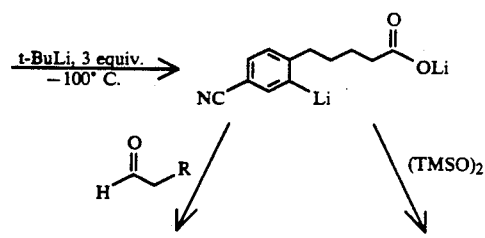
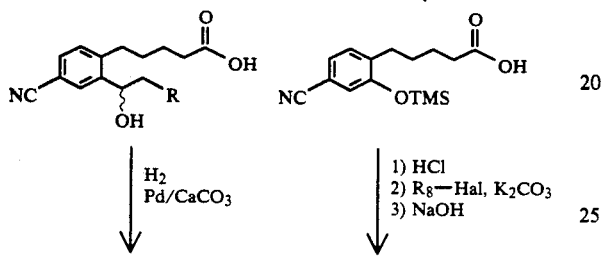
Scheme E
Method 1
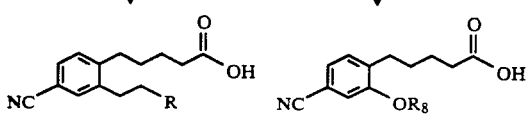
Method 2
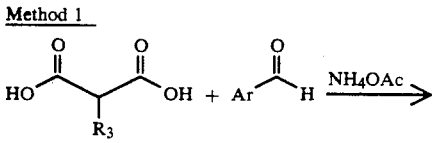
Method 3
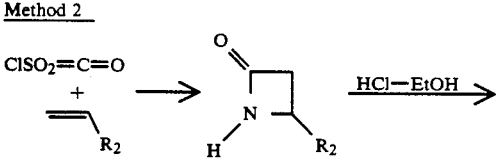
-continued
Scheme E
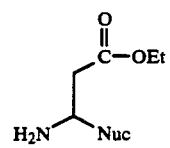
Method 4
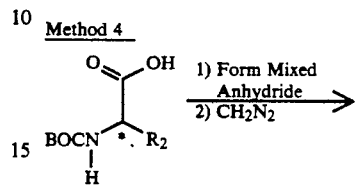
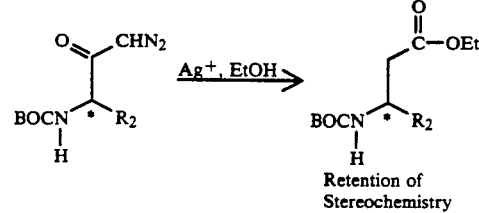
Retention of Stereochemistry
Method 5
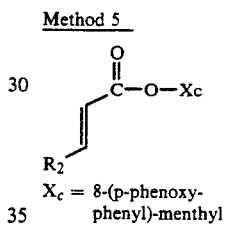
$X_c$ = 8-(p-phenoxy-phenyl)-menthyl
Method 6
Enantioselective Hydrogenation
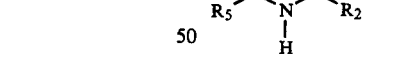
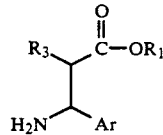
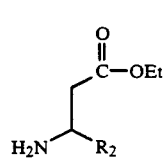
Method 7
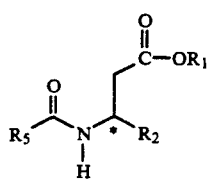
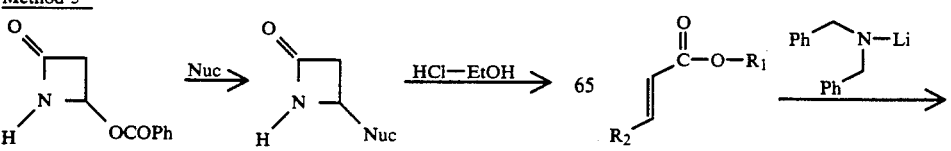

5,272,162
11
-continued
Scheme E
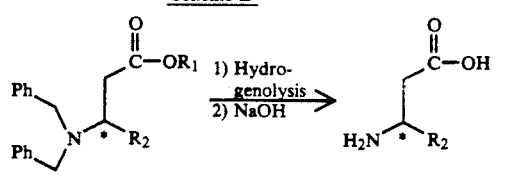
*Indicates Chiral Center
Scheme F
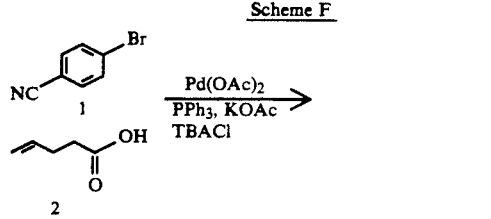
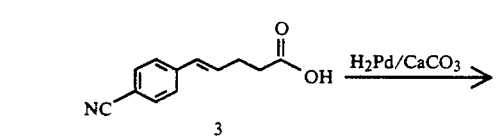
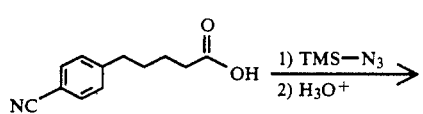
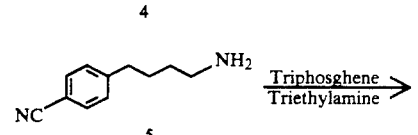
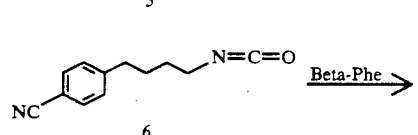
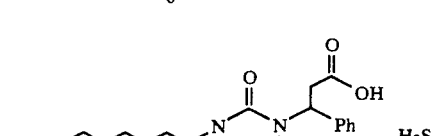
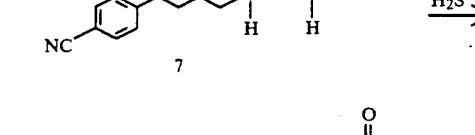
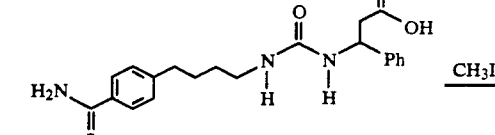
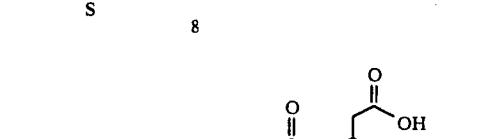
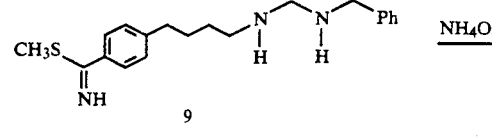
12
-continued
Scheme F
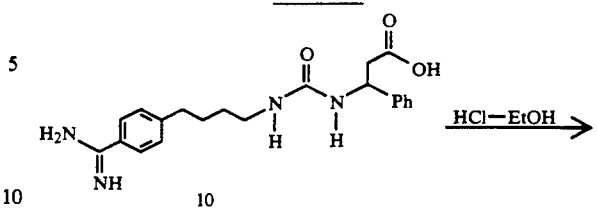
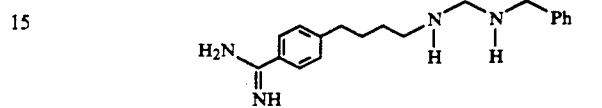
Scheme G
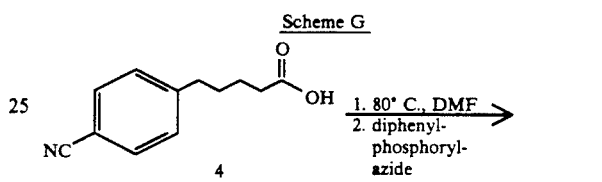
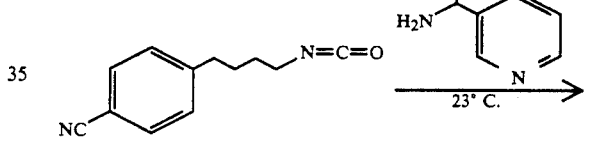
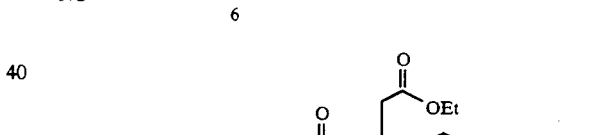
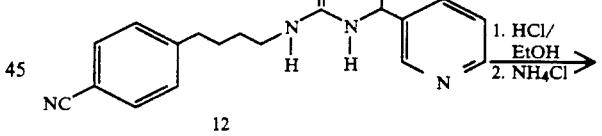
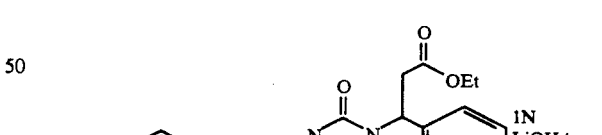
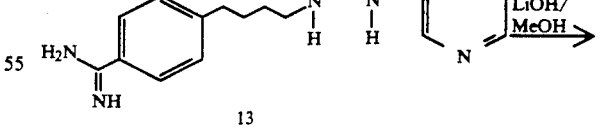
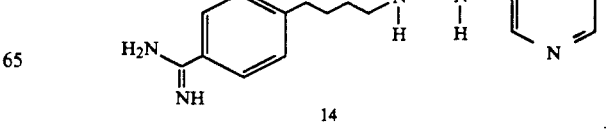

The novel platelet aggregation inhibitors of the present invention can be prepared by methods analogous to solution phase peptide synthesis [see: The Peptides: Analysis, Synthesis, Biology (E. Gross and J. Meienhofer, eds.), Vol. 1-5, Academic Press, New York)] combined with standard synthetic methods. The general synthetic sequence is outlined in Scheme A. The cyano group is converted to the amidine via the thioimidate in nearly quantitative yield. The thioimidate is formed by first treating the cyano compound with hydrogen sulfide ($H_2S$) followed by alkylation with methyl iodide. Next, treatment of the thioimidate with ammonium acetate affords the amidine as the salt (HI). The final compounds for biological testing were obtained by purification by reverse phase high pressure liquid chromatography [High Performance Liquid Chromatography Protein and Peptide Chemistry (F. Lottspeich, A. Henscher, K. P. Hupe, eds.) Walter DeGruyter, New York, 1981].

The benzonitrile urea derivative of Scheme A can be prepared from the corresponding acid derivative using a Curtius rearrangement as outlined in Scheme B. The intermediate isocyanate can be prepared in a three step process using trimethylsilylazide [H. R. Kricheldorf, *Chem. Ber.*, Vol. 105, 3958-3965 (1972)] followed by aqueous hydrolysis to the amine. The amine is converted to the isocyanate by treatment with triphosghene [H. Eckert and B. Forsten, Anqew. Chem. *Int. Ed. Enol.* 894-895 (1987)] and subsequent reaction with the beta amino ester affords the benzonitrile urea of Scheme A. Alternatively, the benzonitrile urea is obtained directly from the corresponding acid by treatment with diphenylphosphorylazide [S. Yamada, K. Ninomiya and T. Shioiri *Tetrahedron Lett.* 2343 (1973); P. A. S. Smith Org. React. Vol. 3, 337 (1946); J. H. Saunders, R. J. Slocombe, *Chem. Rev.*, V. 43, 203 (1948)] followed by trapping the intermediate isocyanate with the beta amino ester.

The benzonitrile acid of Scheme B where A=alkenyl, alkynyl, or alkyl having 2 to 4 carbon atoms can be prepared in the following manner: The halobenzonitrile (Z=H) is coupled to an omega alkynoic (Scheme C-Method I) or alkenoic acid (Scheme C-Method 2) using a palladium(O) based coupling reaction ["Heck Reaction"—Palladium Reagents in Organic Syntheses (Richard F. Heck), Academic Press, New York, 1985].

The preferred conditions for the palladium coupling reaction differed for the alkynoic acid and the alkenoic acid coupling components. When A=alkynyl having 2 to 4 carbon atoms, the preferred conditions for the palladium coupling reaction utilized tetrakis(triphenylphosphine)-palladium(O) as catalyst and piperidine as the solvent [Scheme C-Method 1, for related conditions see: H. A. Dieck and F. R. Heck J. Oroanometallic Chem. 259-263(1975)]. When A=alkenyl having 2 to 4 carbon atoms, the preferred conditions for the alkenoic acid coupling component utilized the phase transfer conditions of Jeffery and Larock [Scheme C-Method 2, T. Jeffery *J. Chem. Soc. Chem. Commun.* 1287-89(1984); R. C.Larock Tetrahedron Lett. 2603-2606 (1989)]. These conditions [phase transfer agent-tetrabutylammonium salt, catalyst-palladium(II) acetate, base-potassium acetate, solvent-dimethyl formamide] are extremely mild conditions which afforded a good yield of coupled olefin. Compounds where A=alkyl were obtained through a selective reduction of the double bond by catalytic reduction over palladium on calcium carbonate.

The required omega alkenoic acids are either commercially available or can be synthesized by oxidation of the omega alkenols [E. J. Corey and G. Schmidt *Tetrahedron Lett.* 399 (1979)]. The required omega alkynoic acids are either commercially available or can be synthesized from the omega haloalkanoic acids and lithium acetylide [W. J. DeJarlais, E. A. Emken *Synthetic Commun.* 653 (1980); J. Cossy, J. P. Pete *Tetrahedron Lett.* 573 (1986)].

An alternative method for the preparation of the (cyanophenyl)alkenoic acid unit (A=alkenyl) can be employed using a standard Wittig reaction (Wittig Reaction-Recent Review- B. E. Maryanoff, A. B. Reitz *Chem Rev.* 863-927 (1989)] with cyanobenzaldehyde and an omega substituted (carboxyalkyl)triphenylphosphonium bromide as the two reaction components (Scheme C-Method 3) [for related conditions see: *J. Am. Chem. Soc.* 397 (1970); Ibid 6831 and 7185 (1973)].

The substituents, Z=halogen, alkyl, hydroxy, or alkoxy, can be introduced where A=alkyl at the benzonitrile stage (e.g. compound 4, Scheme F) using bromine, iodine, or chlorine to halogenate the ring (Scheme D). The alkyl group can be introduced by low temperature lithium halogen exchange followed by quenching with the appropriate aldehyde [see: W. E. Parham, C. K. Bradsher *Acct. Chem. Res.* 300 (1982)]. The resultant alcohol can be converted to Z=alkyl by hydrogenolysis [Reductions in Organic Chemistry (M. Hudlicky, ed.), John Wiley & Sons, New York, 1984] as shown in Scheme D.

The substituents, Z=hydroxy or alkoxy, can be introduced by low temperature lithium halogen exchange followed by quenching with the electrophilic bis(trimethylsilyl)peroxide [$(TMSO)_2$-Scheme D) M. Taddei and A. Ricci *Synthesis* 633-635 (1986)] which affords the silyl ether. The silyl ether can be converted to the Z=OH by treatment with hydrochloric acid [M. Taddei and A. Ricci ibid]. The Z=OR can be formed by treating the derivative where Z=OH with weak base ($K_2CO_3$) and an appropriate alkyl halide [R8-Hal, 2 equivalents, see: C. F. H. Allen and J. W. Gates, Jr. *Organic Syntheses Coll. Vol.* 3 140 (1955)] which Will form the ester as well. The ester can be selectively cleaved in the presence of the ether with one equivalent of sodium hydroxide (Scheme D).

The beta amino acids can be either purchased or prepared from commercially available starting materials using known methods as illustrated in Scheme E. The racemic beta aryl beta amino acids can be prepared from the appropriate aryl aldehyde, malonic acid, and ammonium acetate as shown in Scheme E-Method 1 (Johnson and Livak *J. Am. Chem. Soc.* 299 (1936)]. The racemic beta alkyl beta amino acids can be prepared from the corresponding alkene and chlorosulfonyl isocyanate (CSI) which goes through the beta lactam intermediate as shown in Scheme E-Method 2 [W. A. Szabo *Aldrichimic Acta* 23 (1977); R. Graf Anqew. Chem. Internat. Edit 172 (1968)]. The beta lactam can be opened to the ethyl ester by treatment with anhydrous hydrochloric acid in ethanol as shown Scheme E. For example, 1,3-butadiene was reacted with CSI to form the corresponding vinyl beta lactam and following subsequent opening with anhydrous HCl in ethanol was used in example 11.

An alternative method to form racemic beta amino esters is shown in Scheme E-Method 3. Nucleophiles (Nuc) can be added to 4-benzoyloxy-2-azetidinone to afford a variety of 3-substituted beta amino esters after treatment with anhydrous HCl in ethanol. For example, 1-lithio-2-trimethylsilylethyne was added to 4-benzoyloxy-2-azetidinone to afford the beta amino ester of example 9 after ring opening and treatment with tetrabutylammonium fluoride [for a similar reaction see: D. H. Hua and A. Verma *Tetrahedron Lett.* 547–550 (1985) or T. Kametani, *Heterocycles*, vol. 17 463 (1982)]. 4-benzoyloxy-2-azetidinone was reacted with allyltrimethylsilane under Lewis acid catalysis [titanium tetrachloride- K., Prasad et. al Vol. 19 *Heterocycles* 2099 (1982)].

The racemic beta amino acids can be resolved using classical methods as described in the literature [E. Fischer, H. Scheibler, R. Groh *Ber.* 2020 (1910); E. Fischer, H. Scheibler *Annalen* 337(19II)]. Furthermore, classical chromatographic separation of diastereomeric amides can be used to separate the enantiomers of the racemic beta amino esters. For example, ethyl 3S-amino-1-trimethylsilyl-4-pentynoate was separated by making the diastereomeric O-methylmandelic amide and chromatographic separation as described in the literature for the separation of propargyl amines [B. M. Nilsson and U. Hacksell *Acta Chemica Scandinavica* Vol. B42 55–58 (1988)]. Ethyl 3S-amino-1-trimethylsilyl-4-pentynoate was converted to 3S-amino-4-pentynoate by treatment with tetrabutylammonium fluoride [K. Mikami, K. Kawamoto, T. Nakai *Tetrahedron Lett.* 5799–5802 (1985)] and used in example 9.

Chiral beta amino acids can be prepared using many different approaches including the following methods: homologation of the alpha amino acids using an Arndt-Eistert reaction as shown in Scheme E-Method 4 [Meier and Zeller *AnEew. Chem. Int. Ed. Eng.* 32–43 (1975)] [M. Rodriguez et. al. *Tetrahedron Lett.* 5153 (1990); W. J. Greenlee *J. Med. Chem.* 434 (1985) and references therein]; through the addition of chiral amines to alpha, beta unsaturated esters bearing a chiral auxiliary as shown in Scheme E-Method 5 [J. d'Angelo and J. Maddaluno *J. Am. Chem. Soc.* 8112–14 (1986)]; through an enantioselective hydrogenation of a dehydroamino acid as shown in Scheme E method 6 [see: Asymmetric Synthesis, Vol. 5, (J. D. Morrison, ed.) Academic Press, New York, [1985]; through the addition of enantiomerically pure amines to alpha, beta unsaturated esters as shown in Scheme E-Method 7 [see: S. G. Davies and O. Ichihara *Tetrahedron; Asymmetry* 18314 186 (1991)].

A specific synthesis of the antiplatelet agent (11) is shown in Scheme F and the specific synthesis of (14) is shown in Scheme G. The compound numbers correspond to the compound numbers in example 1. Examples 3–18 were prepared using the method of example 1 or example 2 with the specific changes as stated in each example, and in the general manner described in Schemes A and B. Examples 2–18 further illustrate the nature of the novel compounds in this invention. It will be understood that these novel compounds are not limited to the disclosed methods of making them.

Contemplated equivalents of the platelet aggregation inhibitors, derivatives and intermediates of the formulas set forth above include compounds having the same general properties, wherein one or more of the various R groups are simple variations of the substituents as defined herein, e.g., wherein R is a higher alkyl group than that indicated. In addition, where a substituent can be a hydrogen, a substituent other than hydrogen can be introduced at that position, e.g., a hydrocarbon radical or a halogen, hydroxy, amino and the like, as long as the overall activity and/or synthesis procedure is not affected.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional.

The following examples are provided to illustrate the present invention and are not intended to limit the scope thereof. Those skilled in the art will readily understand that known variations of the conditions and processes of the following preparative procedures can be used to prepare the compounds of the present invention.

EXAMPLE 1

Preparation of

β-[[[[4-[4-(aminoiminomethyl)phenyl]butyl]amino]-carbonyl]amino]benzenepropanoic acid

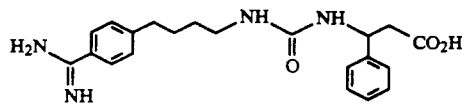

Section A.

5-(p-Cyanophenyl-4-pentenoic acid (3)

Tetrabutylammonium chloride (hydrate, 17.8 g) was dried by azeotroping with benzene (250 mL round bottom flask equipped with a Dean-Stark apparatus). The benzene was removed in vacuo affording anhydrous tetrabutylammonium chloride (17.0 g, 61.2 mmol). To this flask under argon were added triphenylphosphine (820 mg, 3.13 mmol), palladium acetate (703 mg, 3.13 mmol), 4-bromobenzonitrile (16.9 g, 92.8 mmol), potassium acetate (36.8 g, 375 mmol) and 100 mL of degassed anhydrous dimethylformamide (degassed by bubbling argon through for 10 min, dried over molecular sieves). A solution of 4-pentenoic acid (6.27 g, 62.6 mmol) and degassed anhydrous DMF (35 mL) was then added to the rapidly stirring reaction mixture at 23° C. After 21 hours at 23° C., the reaction mixture was poured slowly into a sodium carbonate solution (3%, 400 mL) and extracted with ethyl acetate (500 mL). The aqueous layer was treated with decolorizing carbon, and filtered. Then, the aqueous layer was acidified to a pH of 2 with 10% HCl which afforded a White solid (6.82 g, 54%): m.p. 150°–167° C.

The above procedure affords (3) in sufficient purity to take on to the next step without complications. An analytical sample was obtained by submitting the sample to further purification by flash chromatography (ethyl acetate:methylene chloride:acetic acid, 1:4:0.05) and recrystallization from ethyl acetate (2 times): m.p. 154°–156° C.

Anal. Calcd. for $C_{12}H_{11}NO_2$: C, 71.63; H, 5.51; N, 6.96.

Found: C, 71.50; H, 5.54; N, 6.80.

Section B

5-(p-Cyanophenyl)pentanoic acid (4)

A solution of 1.47 g (7.32 mmol) of (3) in 90 mL of methanol was hydrogenated over 200 mg of 5% Pd/CaCO$_3$ at 5 psi hydrogen over a 1.2 hour period. After removing the catalyst by filtration and evaporation of the solvent in vacuo, the residue was triturated with ether followed by hexane which afforded a white solid: m.p. 101°-102° C.

Anal. Calcd. for C$_{12}$H$_{13}$NO$_2$: C, 70.92; H, 6.45; N, 6.89.

Found: C, 70.71; H, 6.56; N, 6.87.

Section C

5-(p-Cyanophenyl)pentylamine

Oxalyl chloride (43.0 mL, 0.492 mol) was added dropwise to a suspension of 5-(p-cyanophenyl)pentanoic acid in 100 mL of dry 1,2-dichloroethane at 23° C. under a nitrogen atmosphere. After 5 min, 50 mL of DMF was added. After 30 min, the reaction was concentrated in vacuo. The residue was dissolved in anhydrous THF (150 mL) under a nitrogen atmosphere. Azidotrimethylsilane (14.6 mL, 0.110 mL) was added dropwise at 23° C. After 5 min, the reaction was warmed to achieve reflux for 1 hour. The reaction was cooled to 10° C. and concentrated HCl (20 mL) was added over 1 min. The cooling bath was removed and stirring was continued for 15 min. The reaction was concentrated in vacuo and the residue was partitioned between ethyl acetate (200 mL) and water (200 mL). The aqueous layer was basified with 1 N NaOH (250 mL) and extracted with ethyl acetate (2×200 mL). The organic layer was washed with water (100 mL) followed by brine (100 mL), and dried (Na$_2$SO$_4$). After concentration in vacuo, the residue was diluted with ethyl acetate:methanol (150 mL:5 mL) and treated with anhydrous HCl in dioxane (6.9 N) at 0° C. The resultant precipitate was filtered, washed with ethyl acetate then ether. The solid was dried (atmospheric pressure; 55° C.) to afford 14.3 g: m.p. 155°-160° C.

Anal. Calcd. for C$_{11}$H$_{15}$N$_2$CL: C, 62.70; H, 7.18; N, 13.30. Found: C, 62.76; H, 7.35; N, 13.34.

Section D

β-[[[[4-Cyanophenyl]butyl]amino]carbonyl]aminobenzenepropanoic acid

A solution of amine hydrochloride (5) (1.00 g, 4.74 mmol), triphosghene (0.469 g, 1.58 mmol), triethylamine (1.27 g, 12.6 mmol), and dioxane (20 mL) was warmed to 70° C. for 2 hours under an argon atmosphere. After cooling to 23° C., the reaction mixture was diluted with ethyl acetate (80 mL), filtered, and concentrated under a stream of nitrogen in the hood to afford the intermediate isocyanate (6).

A solution of the isocyanate (6) (4.74 mmol), triethylamine (0.479 g, 4.74 mmol), β-phenylalanine (1.17 g, 7.11 mmol), and anhydrous DMF (10 mL) was warmed to 120° C. for 20 hours. After cooling to 23° C., the reaction mixture was concentrated on the rotovap, diluted with ethyl acetate (400 mL), washed with KHSO$_4$ (1 N, 2×100mL), washed with brine (1×100 mL), and dried (Na$_2$SO$_4$). After concentration in vacuo. The urea was purified by flash chromatography (step gradient ethyl acetate with 1% acetic acid to ethyl acetate with 10% methanol and 1% acetic acid) to afford 1.49 g (86%) of (7).

Section E

β-[[[[4-[4-(aminoiminomethyl)phenyl]butyl]amino]-carbonyl]amino]benzenepropanoic acid Hydrogen sulfide was bubbled (under a hood) through a solution of 1.49 g (4.08 mmol) of (7) in pyridine:triethylamine (24 mL:2.4 mL) for 3 min at 23° C. After 24 hours at 23° C. in an enclosed flask, the reaction mixture was concentrated under a steady stream of nitrogen. The residue was diluted with ethyl acetate (200 mL), washed with KHSO$_4$ (2N, 2×50 mL), brine (1×50 mL), and dried (Na$_2$SO$_4$). Concentration in vacuo afforded a quantitative yield of thioamide (8).

Thioamide (8) (4.08 mmol) was dissolved in a solution of acetone:iodomethane (14 mL:1mL). The reaction mixture was warmed to achieve reflux for 25 min. Concentration in vacuo afforded a quantitative yield of (9) as the HI salt.

A solution of (9) (4.08 mmol) and ammonium acetate (472 mg, 6.12 mmol) in methanol (10 mL) was warmed to achieve reflux for 3.5 hours. After cooling to 23° C., the reaction mixture was concentrated under a steady stream of nitrogen in the hood which afforded a quantitative yield of (10). The product was purified on a Waters reverse-phase C-18 microbondapak column (5 cm×30 cm) using a linear gradient of 5% acetonitrile/water 0.05% trifluoracetic acid to 40% acetonitrile/water 0.05% trifluoroacetic acid (30 min) with a flow rate of 80 mL/min to afford (10). The product purity was verified by C NMR (CD$_3$OD) delta 27.8, 29.4, 34.9, 39.2, 41.2, 50.8, 125.4, 125.9, 126.9, 127.6, 128.2, 129.0, 142.5, 149.6, 159.9, 166.9, 173.2.

Anal. Calcd. for C$_{21}$H$_{26}$N$_4$O$_3$ plus 0.6 H$_2$O and 1.0 trifluoroacetic acid: C, 54.46; H, 5.60; N, 11.04.

Found: C, 54.45; H, 5.27; N, 11.02.

EXAMPLE 2

Preparation of ethyl β-[[[[4-[4-(aminoiminomethyl)phenyl]butyl]-amino]carbonyl]amino]benzenepropanoate

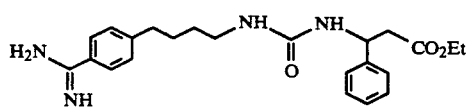

Compound (10) was esterified in neat ethanol saturated with anhydrous hydrochloric acid to afford (11) after concentration in vacuo. The final product was purified in the manner of Example 1E. The product was verified by C NMR (CD$_3$OD) delta 13.7, 27.9, 29.0, 35.2, 40.7, 41.2, 52.1, 60.9, 125.2, 126.5, 127.8, 128.1, 128.7, 129.5, 141.1, 149.7, 159.0, 166.7, 170.9.

EXAMPLE 3

Preparation of ethyl β-[[[[4-[4-(aminoiminomethyl)phenyl]-butyl]amino]carbonyl]amino]-3-pyridinepropanoate

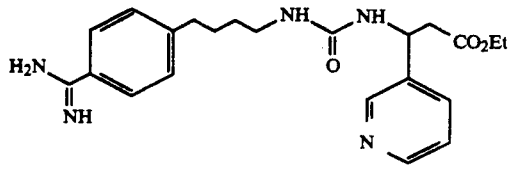

Section A 4-cyanophenylpentanoic acid (1.1 g; 5 mmoles) was dissolved in DMF (50 ml) and the solution was heated to 90° C. To this mixture, diphenylphosphorylazide (1.4 g; 5 mmoles) and N,N-diethyl-N-isopropylethylamine (2 g; 15 mmoles) were added slowly with stirring. After 2 hours, the heating was discontinued and ethyl-3-amino-3-(3-pyridyl)propanoate HCl (1 g; 5 mmoles) dissolved in DMF (20 ml) was added. The mixture was stirred for another 3 hours and taken down to dryness on rotavapor. The residue was dissolved in acetonitrile/water and purified on a C-18 HPLC column (30 cm×5 cm) with a flow rate of 80 ml/min. A linear gradient of 15 to 40% acetonitrile/water/0.05% TFA in 30 min. and 40 to 60% in 5 min. was used. The ester eluted at 40% acetonitrile concentration and the desired peak was lyophilized to yield 500 mg of white solid (FAB-MS: MH+ =395).

Section B

Ethyl β-[[[4-[4-cyanophenyl]butyl]amino]carbonyl]amino]-3-pyridinepropanoate (500 mg; 1 mmoles) was treated with HCl gas/ethanol (100 ml) in an ice bath for 1 hour. The reaction mixture was stirred at room temperature overnight. The solvent was removed on rotavapor and the residue was redissolved in ethanol (200 ml). Ammonium chloride (0.5g) and ammonium hydroxide (3ml in 10 ml H2O) were added with vigorous stirring. The reaction mixture was gently refluxed overnight and taken down to dryness on a rotavapor. The residue was purified on a C-18 HPLC column as described above. A linear gradient of 10 to 40% acetonitrile/water/0.05% TFA in 30 min. and 40 to 60% in 5 min. was used. The ester eluted at 23% acetonitrile concentration and the desired peak was lyophilized to yield 200 mg of white solid (FAB-MS: MH+ =412).

| Elemental analysis: $C_{22}H_{29}N_5O_3.TFA.2H_2O$ | | | |
|---|---|---|---|
| | C | H | N |
| Calculated: | 51.33 | 6.10 | 12.47 |
| Found: | 50.84 | 6.29 | 12.81 |

EXAMPLE 4

β-[[[[4-[4-(aminoiminomethyl)phenyl]butyl]amino]carbonyl]amino]-3-pyridinepropanoic acid

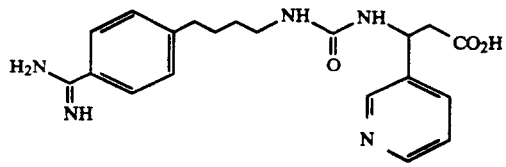

ethyl β-[[[[4-[4-(aminoiminomethyl)phenyl]butyl]amino]carbonyl]amino]-3-pyridinepropanoate TFA (100 mg; 2 mmol), methanol (5ml), and 2N LiOH (5ml) were stirred for 30 min. The solution was acidified to pH=3 with 3N HCl and reduced to dryness on a rotary evaporator. The residue was dissolved in acetonitrile/water and purified by HPLC on a C-18 HPLC column (30cm×5cm). A gradient of 10 to 40% acetonitrile/water/ 0.05% TFA in 30 min. was used and the acid eluted at an acetonitrile concentration of 15%. Fractions containing the desired peak were lyophilized to give 70 mg of white solid. FAB-MS: MH+ =384.

| Elemental analysis: $C_{20}H_{25}N_5O_3.2CF_3COOH.2H_2O$ | | | |
|---|---|---|---|
| | C | H | N |
| Calculated: | 44.52 | 4.82 | 10.81 |
| Found: | 44.77 | 4.18 | 10.72 |

EXAMPLE 5

Preparation of 3-[[[[4-[4-(aminoiminomethyl)phenyl]butyl]amino]-carbonyl]amino]butanoic acid

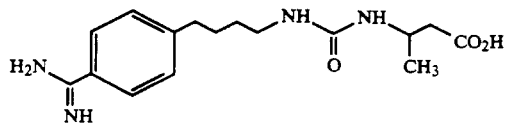

The title compound was prepared in the manner of Example 1 with the following modifications: Substituting 3-methyl-beta-alanine for 3-phenyl-beta-alanine. The product was verified by C NMR (CD3OD) delta 19.7, 27.9, 29.4, 34.9, 39.1, 40.8, 42.8, 125.5, 127.6, 129.1, 149.7, 159.0, 167.0, 173.7.

EXAMPLE 6

Preparation of 5-(p-cyanophenyl)-4-pentynoic acid

A solution of 4-pentynoic acid (2.15 g, 22 mmol), 4-bromobenzonitrile (3.64 g, 20 mmol), and piperidine (40 mL) was degassed by bubbling nitrogen through the solution for 5 min. prior to the addition of tetrakis(triphenylphosphine) palladium(0) (240 mg, 0.2 mmol). The reaction vial was sealed and warmed to 80° C. for 1.5 hours. After cooling to 23° C., the reaction mixture was diluted with ethyl acetate (200 mL), filtered, and concentrated in vacuo. The residue was diluted with ethyl acetate (300 mL), washed with 5% HCl (2×100 mL), washed with water (1×100 mL), and extracted with 3% sodium carbonate (2×200 mL). The basic aqueous layer was treated with decolorizing carbon, filtered, and acidified to pH=2. The resultant solid was filtered, washed with water, dried, and purified by flash chromatography (gradient ethyl acetate:methylene chloride:acetic acid 1:9:0.005) and fractional recrystallization (methylene chloride-ether) to afford 5-(p-cyanophenyl)-4-pentynoic acid as a white solid: m.p. 149°–152° C.

Anal Calcd. for $C_{12}H_9NO_2$: C, 72.35; H, 4.55; N, 7.03.

Found: C, 72.05; H, 4.57; N, 6.94.

EXAMPLE 7

Preparation of

β-[[[[4-[4-(aminoiminomethyl)phenyl]-1-butynyl]amino]carbonyl]amino]-benzenepropanoic acid The title compound can be prepared in the manner of Example 1 with the following modification: the 5-(p-cyanophenyl)-4-pentynoic acid as prepared in Example 6 is substituted for 5-(p-cyanophenyl)pentanoic acid in Section C of Example 1. The product is purified by reverse phase HPLC using the conditions of Example 1 to afford the title compound. The product is verified by C NMR and Chemical Ionization Mass Spectrometry.

EXAMPLE 8

β-[[[[4-[4-aminoiminomethyl)phenyl]-1-butenyl]amino]carbonyl]amino]benzenepropanoic acid The title compound can be prepared in the manner of Example 1, but the reduction step is omitted (Section B). The product is purified by reverse phase HPLC using the conditions of Example 1 to afford the title compound. The product is verified by C NMR and Chemical Ionization Mass Spectrometry.

EXAMPLE 9

Preparation of ethyl 3S-[[[[4-[4-aminoiminomethyl]phenyl]butyl]amino]carbonyl]amino]-4-pentynoate

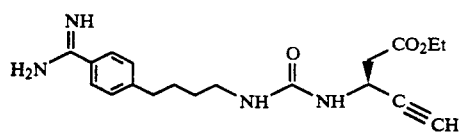

The title compound was prepared in the manner of Example 1 with the following modifications: Substituting ethyl 3S-amino-4-pentynoate for 3-phenyl-beta-alanine. The ethyl 3S-amino-4-pentynoate was prepared in an analogous manner to the literature precedent as described above and the structure was verified by C NMR of the hydrochloride salt (CDCl$_3$) delta 13.8, 37.1, 39.7, 61.6, 64.7, 67.2, 169.2. Analysis of the beta amino ester by chiral HPLC using a crownpak ether column [CR(+)] cooled to 5° C. using methanol:water 10:90 at pH of 1 (HClO$_4$) and a flow rate of 0.5 mL/min showed an enantiomeric ratio of 98:2. The title compound was verified by C NMR (CD$_3$OD) delta 13.6, 28.4, 35.4, 39.1, 39.7, 41.0, 61.0, 71.4, 82.9, 127.0, 128.5, 129.8, 150.1, 158.6, 166.8, 170.8. Fast Atom Bombardment Mass Spectrometry (MH+ =359).

EXAMPLE 10

Preparation of

3S-[[[[4-[4-(aminoiminomethyl)phenyl]butyl]amino]carbonyl]amino]-4-pentynoic acid

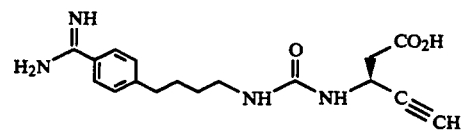

Porcine liver esterase (400 μL, Sigma, 11 mg/mL in 3.2 M (NH$_4$)$_2$SO$_4$ at pH=8) was added to the final product of example 9 in 30mL of 0.1 M phosphate buffer (pH=7.4). After 20 hours at 23° C., the reaction mixture was concentrated in vacuo. The residue was dissolved in 1N HCl (3 mL) and subsequently diluted with acetonitrile (5 mL) followed by immediate purification by reverse phase HPLC using the conditions of example 1 to afford 60 mg of the title compound. The product was verified by C NMR (CD$_3$OD) delta 28.5, 30.0., 35.5, 39.1, 39.8, 40.8, 71.2, 83.4, 126.5, 128.2, 129.7, 150.5, 158.7, 167.5, 172.8.

Fast Atom Bombardment Mass Spectrometry (MH+ =331).

EXAMPLES 11

Preparation of ethyl 3S-[[[[4-[4-(aminoiminomethyl)phenyl]butyl]amino]carbonyl]amino]-4-pentenoate

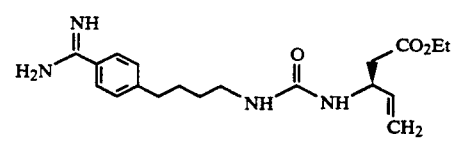

The title compound was prepared in the manner of Example 1 with the following modifications: Substituting ethyl 3S-amino-4-pentenoate for 3-phenyl-beta-alanine. The ethyl 3S-amino-4-pentenoate was prepared in an analogous manner to the literature precedent as described above and the structure was verified by C NMR of the hydrochloride salt (CDCl$_3$) delta 14.9, 37.7., 51.4, 62.2, 121.9, 133.1, 171.0. Analysis of the beta amino ester by chiral HPLC using a crownpak ether column [CR(+)] cooled to 5° C. using methanol:water 10:90 at pH of 1 (HClO$_4$) and a flow rate of 0.5 mL/min showed an enantiomeric ratio of 100:0, [α]589-7.1 (c, CH$_2$Cl$_2$). The title compound was verified by C NMR (CD30D) delta 13.7, 28.5, 30.0, 35.5, 39.7, 40.0, 49.4, 60.8, 114.4, 128.1, 129.7, 138.6, 150.2, 159.8, 166.8, 171.8.

Fast Atom Bombardment Mass Spectrometry (MH+ =361).

EXAMPLE 12

Preparation of

3S-[[[[4-[4-(aminoiminomethyl)phenyl]butyl]amino]carbonyl]amino]-4-pentenoic acid

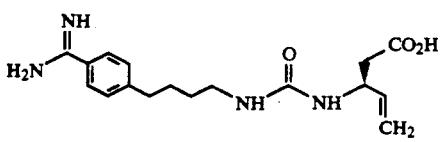

Procine liver esterase (400 μL, Sigma, 11 mg/mL in 3.2 M $(NH_4)_2SO_4$ at pH=8) was added to the final product of example 11 in 20mL of 0.1 M phosphate buffer (pH=7.4). After 20 hours at 23° C., the reaction mixture was concentrated in vacuo. The residue was dissolved in 1N HCl (3 mL) and subsequently diluted with acetonitrile (5 mL) followed by immediate purification by reverse phase HPLC using the conditions of example 1 to afford 68.0 mg of the title compound. The product was verified by C NMR (DSMO-d6) delta 28.5, 30.2, 35.2, 48.9, 114.3, 126.2, 128.7, 129.5, 140.0, 149.5, 157.9, 166.2, 172.8.

Fast Atom Bombardment Mass Spectrometry (MH+ =333).

[α]589+17.1 (c 0.67, $CH_3OH$).

Anal. Calcd. for $C_{17}H_{24}N_4O_3$ plus 1.1 $CF_3CO_2H$ and 1.0 $H_2O$;

C,48.46; H,5.74; N,11.77. Found: C,48.29; H,5.33; N,11.55.

EXAMPLE 13

Preparation of ethyl 3-[[[[4-[4-(aminoiminomethyl)phenyl]butyl]amino]carbonyl]amino]propanoate

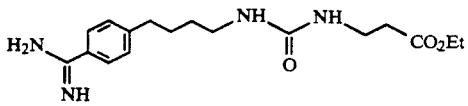

The title compound was prepared in the manner of Example 1 with the following modifications: Substituting ethyl beta-alanine for 3-phenyl-beta-alanine. The title compound was verified by H NMR (DMSO-D6) delta 1.17 (t, J=6Hz,$CH_3$), 1.31-1.62 (m,$CH_2CH_2$),2.39(t,J=6Hz,$CH_2$),2.68(t,J=6Hz,$CH_2$), 2.98(dt,J=5.5 and 6Hz,$CH_2$NH),3.19(dt,J=5.5 and 6Hz,$CH_2$NH),4.04(q,J=6Hz,$CH_2$)5.84(t,J=5.5Hz,NH-), 5.96(t,J=5.5Hz,NH),7.45(d,J=7.5Hz,$PhH_2$)7.73 (d,J=7.5Hz,$PhH_2$),8.90(bs,NH),9.23(bs,NH). Anal. Calcd. for $C_{17}H_{26}N_4O_3$ plus 1.1 $CF_3CO_2H$ and 1.0 $H_2O$: C,48.26; H, 6.14; N,11.72. Found: C,48.12; H,5.51; N,11.56.

EXAMPLE 14

Preparation of

3-[[[[4-[4-(aminoiminomethyl)phenyl]butyl]amino]carbonyl]amino]propanoic acid, monohydrochloride

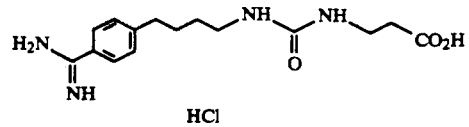

The title compound was prepared by hydrolyzing the ester of Example 13 by treatment with 6N HCl:dioxane (1:1) for 20 hours at 23° C. Concentration in vacuo afforded the title compound as the hydrochloride salt. The title compound was verified by H NMR ($CD_3OD$) delta 1.52-1.82 (m,$CH_2$ $CH_2$ ),2.66(t,J=6Hz,$CH_2$)2.78(t,J=6Hz,$CH_2$), 3.30-3.40(m,$CH_2$),3.75(t,J=6Hz,$CH_2$),7.45(d,J=7.5Hz,$PhH_2$), 7.73(d,J=7.5Hz,$PhH_2$),8.70(bs,NH),9.18(bs,NH).

EXAMPLE 15

Preparation of ethyl 3-[[[[4-[4-(aminoiminomethyl)phenyl]butyl]amino]carbonyl]amino]-5-hexenoate

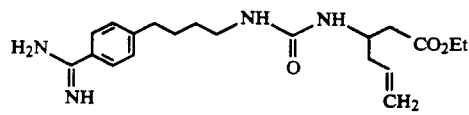

The title compound was prepared in the manner of Example 1 with the following modifications: Substituting ethyl 3-amino-5-hexenoate for 3-phenyl-beta-alanine. The title compound was verified by H NMR ($CD_3OD$) delta 1.22(t,J=6Hz,$CH_3$)1.45-1.72(m,$CH_2$ $CH_2$ ),2.22-2.31(m,$CH_2$), b 2.42-2.51(m,$CH_2$),2.72(m,CH),3.13(t,J=6Hz, $CH_2$NH), 4.10(q,J=6Hz,$CH_2$),5.03-5.12(m,=$CH_2$),5.72-5.85 (m,=CH), 7.46(d,J=7.5Hz,$PhH_2$),7.73(d,J=7.5Hz,$PhH_2$).

EXAMPLE 16

Preparation of

3-[[[[4-[4-(aminoiminomethyl)phenyl]butyl]amino]carbonyl]amino]-5-hexenoic acid

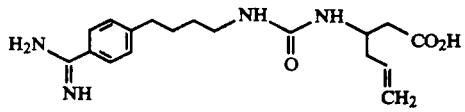

The title compound was prepared by hydrolyzing the ester of Example 15 by treatment with 6N HCl:dioxane (1:1) for 20 hours at 23° C. Concentration in vacuo afforded the title compound as the hydrochloride salt. The title compound was verified by H NMR ($CD_3OD$) delta 1.52-1.72 (m,$CH_2$ $CH_2$ ),2.25-2.47(m,$CH_2$),2.-50-2.57(m,$CH_2$), 2.781-2.81(m,$CH_2$),3.19(t,J=6Hz,$CH_2$),5.-05-5.16(m,=$CH_2$), 5.72-5.85(m,=CH),7.45(d,J=7.5Hz,PhH$_2$),7.73 (d,J=7.5Hz,PhH$_2$),8.70(bs,NH),9.18(bs,NH).

EXAMPLE 17

Preparation of ethyl 3-[[[[4-[4-cyanophenyl]-1-butyl]amino]carbonyl]amino]isobutanoate

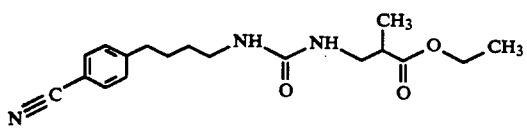

The title compound was prepared in the manner of Example 1 Sections A-D with the following modifications: Substituting ethyl 3-aminoisobutanoate for 3-phenyl-beta-alanine. The title compound was verified by H NMR (CDCl$_3$) delta 1.18(d,J=7Hz,CH$_3$)1.24 (t,J=6Hz,CH$_3$),1.45-1.72(m,CH$_2$ CH$_2$),2.42-2.57(m,CH), 2.49(t,J=6Hz,CH$_2$),2.68(t,J=6Hz,CH$_2$),3.18(dt,J=5.5 and 6Hz,CH$_2$NH),4.13 (q,J=6Hz,CH$_2$),4.44(bt,J=5.5Hz,NH), 4.82(m,NH), 7.27(d,J=7.5Hz,PhH$_2$),7.57(d,J=7.5Hz,PhH$_2$).

EXAMPLE 18

Preparation of ethyl 3-[[[[4-[4-(aminoiminomethyl)phenyl]-1-butyl]amino]-carbonyl]amino]isobutanoate

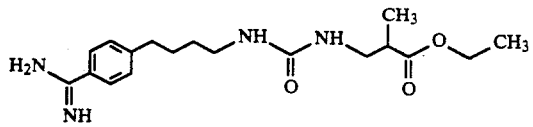

The title compound can be prepared in the manner of example 1 with the following modification: Ethyl 3-[[[[4-[4-cyanophenyl]-1-butyl]amino]carbonyl]amino]-isobutanoate is substituted for β-[[[[4-[4-cyanophenyl]-butyl]amino]-carbonyl]aminobenzenepropanoic acid in Section E of example 1. The product is purified by reverse phase HPLC using the conditions of example 1 to afford the title compound. The product is verified by C NMR and Chemical Ionization Mass Spectrometry.

The platelet-binding inhibitor activity of the compounds of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129 M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2-3×10$^8$ platelets per ml. 400 μl of the PRP preparation and 50 μl of the compound to be tested or saline were preincubated for 1 minute at 37° C. in a BioData aggregometer (BioData, Horsham, PA). 50 μl of adenosine 5'-diphosphate (ADP) (50 μm final concentration) was added to the cuvettes and the aggregation was monitored for 1 minute. All compounds are tested in duplicate. Results are calculated as follows:

Percent of control=[(maximal OD minus initial OD of compound) divided by (maximal OD minus initial OD of control saline)] ×100. The % inhibition=100−(percent of control).

The assay results for the compounds of Examples 1-16 and their median inhibitory concentrations (IC$_{50}$) are recorded in Table I. IC$_{50}$'s (if a compound showed 50% inhibition) were calculated by linear regression of the dose response curve.

INHIBITION OF EX VIVO COLLAGEN INDUCED AGGREGATION BY COMPOUNDS OF THE INVENTION

The purpose of this assay is to determine the effects of antiplatelet compounds on ex vivo collagen induced platelet aggregation when administered orally to dogs.

Pretreatment (control) blood samples are drawn from either conscious or anesthetized dogs (Beagles) and centrifuged to prepare platelet rich plasma (PRP). Aggregatory response to collagen is measured in an aggregometer and used as control. Compounds are administered intragastrically (either by capsule or stomach tube). Blood samples are drawn at predetermined intervals after compound administration, PRP prepared and aggregation to collagen determined. Compound inhibition of aggregation is determined by comparing the aggregation response after compound administration to the pretreatment response. The study is continued for a maximum of 24 hours or until the platelet aggregation returns to control levels. (If aggregation is still inhibited after 7 hours, a blood sample is drawn the following morning and tested.) Duration of activity is determined by the length of time platelet aggregation is inhibited after compound administration. The assay results for representative compounds of the present invention are set forth in Table I.

In Table I the designation "NT" means "Not Tested."

TABLE I

| Example | Dog PRP IC$_{50}$ Micro M | Ex-Vivo Collagen Induced Aggregation | | |
|---|---|---|---|---|
| | | Dose (mg/kg) | Max % Inhibition | Duration (Hrs.) |
| 1 | 0.6 | NT | NT | NT |
| 2 | 20 | 20 | 92 | 2 |
| 3 | 30 | 10 | 70/96 | 7<< |
| 4 | 0.11 | NT | NT | NT |
| 5 | 0.80 | NT | NT | NT |
| 9 | NT | NT | NT | NT |
| 10 | 50 | NT | NT | NT |
| 11 | NT | NT | NT | NT |
| 12 | 0.3 | NT | NT | NT |
| 13 | NT | NT | NT | NT |
| 14 | 48 | NT | NT | NT |
| 15 | NT | NT | NT | NT |
| 16 | 3.1 | NT | NT | NT |

What is claimed is:

1. A compound of the formula

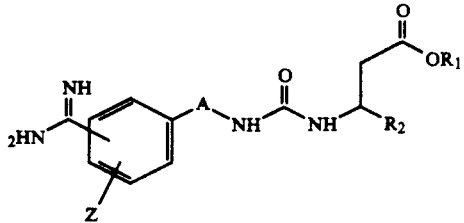

or a pharmaceutically acceptable salt thereof wherein Z is selected from the group consisting of H, halogen, hydroxy, alkoxy of from one to six carbon atoms and alkyl of from one to six carbon atoms; wherein A is selected from the group consisting of alkylene of one to six carbon atoms, alkenylene of two to six carbon atoms and alkynylene of two to six carbon atoms; wherein $R_1$ is selected from the group consisting of H, alkyl of one to six carbon atoms, aralkyl and alkanoyloxyalkyl; and wherein $R_2$ is selected from the group consisting of H, alkyl of one to six carbon atoms, alkenyl of from two ti six carbon atoms, alkynyl of from two to six carbon atoms, aryl and heteroaryl wherein the heteroatom is N all optionally substituted by a radical selected from the group optionally of halogen, alkyl of one to sic carbon atoms, alkoxy of one to six carbon atoms, carboxyl derivatives, nitro, cyano, axido, ureido, ureylene, alkoxycarbonyloxy, hydroxyl, alkylamino, alkoxycarbonyl, triakylsilyl, alkoxyimino, alkysulfonyl, phenylsulfonyl and amino.

2. A compound according to claim 1 wherein
Z is hydrogen;
A is alkylene of one to six carbon atoms;
$R_1$ is selected from the group consisting of hydrogen and alkyl of one to six carbon atoms; and
$R_2$ is selected from the group consisting of hydrogen, alkyl of one to six carbon atoms, alkenyl of two to six carbon atoms and alkynyl of two to six carbon atoms all optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

3. A compound according to claim 2 wherein $R_2$ is methyl.

4. A compound according to claim 3 which is 3-[[[[4-[4-(aminoiminomethyl)phenyl]butyl]amino]carbonyl]amino]butanoic acid.

5. A compound according to claim 2 wherein $R_2$ is vinyl.

6. A compound according to claim 2 wherein $R_2$ is H.

7. A compound according to claim 2 wherein $R_2$ is allyl.

8. A compound according to claim 1 wherein
Z is hydrogen;
A is alkylene of one to sic carbon atoms;
A is alkylene from the group consisting of hydrogen and alkyl of one to six carbon atoms; and
$R_2$ is aryl optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

9. A compound according to claim 8 wherein $R_2$ is phenyl.

10. A compound according to claim 9 which is ethyl β-[[[[4-[4-(aminoiminomethyl)phenyl]butyl]amino]carbonyl]amino]benzenepropanoate.

11. A compound according to claim 9 which is β-[[[[4-[4-(aminoiminomethyl)phenyl]butyl]amino]carbonyl]amino]benzenepropanoic acid.

12. A compound according to claim 1 wherein
Z is hydrogen;
A is alkylene of one to six carbon atoms;
$R_1$ is selected from the group consisting of hydrogen of one to six carbon atoms; and $R_2$ is heteroaryl optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

13. A compound according to claim 12 wherein $R_2$ is pyridyl.

14. A compound according to claim 13 which is ethyl β-[[[[4-[4-(aminoiminomethyl)phenyl]butyl]amino]carbonyl]amino]-3-pyridinepropanoate.

15. A compound according to claim 13 which is β-[[[[4-[4-(aminoiminomethyl)phenyl]butyl]amino]carbonyl]amino]-3-pyridinepropanoic acid.

16. A pharmaceutical composition comprising a compound of the formula

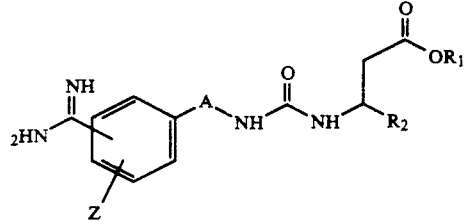

or a pharmaceutically acceptable salt thereof wherein Z is selected from the group consisting of H, halogen, hydroxy, alkoxy of from one to six carbon atoms and alkyl of from one to sic carbon atoms;

wherein A is selected from the group consisting of alkylene of one to six carbon atoms, alkyenylene of two to six carbon atoms and alkynylene of two to six carbon atoms;

wherein $R_1$ is selected from the group consisting of H, alkyl of from one to six carbon atoms, aralkyl and alkanoyloxyalkyl; and wherein $R_2$ is selected from the group consisting of H, alkyl of from one to six groups atoms, alkenyl of from two to six carbon atoms, alkynyl of from two to six carbon atoms, aryl and heteroaryl wherein the heteroatom is N optionally substituted by a radical selected from the group consisting of halogen, alkyl of one to six carbon atoms, alkoxy of one to six carbon atoms, carbonyl derivatives, nitro, cyano, axido, ureido, ureylene, alkoxycarbonyloxy, hydroxyl, alkylamino, alkoxycarbonyl, trialkylsilyl, alkoxyimino, alkylsulfonyl, phenylsulfonyl and amino and a pharmaceutically acceptable carrier.

17. A pharmaceutical composition according to claim 16 wherein

Z is hydrogen;

A is alkylene of one to six carbon atoms;

$R_1$ is selected from the group consisting of hydrogen and alkyl of one to six carbon atoms; and $R_2$ is selected from the group consisting of hydrogen, alkyl of one to six carbon atoms, alkenyl of two to six carbon atoms and alkynyl of two to six carbon atoms all optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

18. A pharmaceutical composition according to claim 17 wherein $R_2$ is methyl.

19. A pharmaceutical composition according to claim 18 wherein the compound is 3-[[[[4-[4-(aminoiminomethyl)phenyl]butyl]amino]carbonyl]amino]butanoic acid.

20. A pharmaceutical composition according to claim 17 wherein $R_2$ is vinyl.

21. A pharmaceutical composition according to claim 17 wherein $R_2$ is H.

22. A pharmaceutical composition according to claim 17 wherein $R_2$ is allyl.

23. A pharmaceutical composition according to claim 16 wherein

Z is hydrogen;

A is alkylene of one to six carbon atoms;

$R_1$ is selected from the group consisting of hydrogen and alkyl of one to six carbon atoms; and $R_2$ is aryl optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

24. A pharmaceutical composition according to claim 23 wherein $R_2$ is phenyl.

25. A pharmaceutical composition according to claim 24 wherein the compound is ethyl β-[[[[4-[4-(aminoiminomethyl)phenyl]butyl]amino]carbonyl]amino]benzenepropanoate.

26. A pharmaceutical composition according to claim 24 wherein the compound is β-[[[[4-[4-(aminoiminomethyl)phenyl]butyl]amino]carbonyl]amino]benzenepropanoic acid.

27. A pharmaceutical composition according to claim 16 wherein

Z is hydrogen;

A is alkylene of one to six carbon atoms;

$R_1$ is selected from the group consisting of hydrogen of one to six carbon atoms; and $R_2$ is a heteroaryl optionally substituted by all optionally substituted by a radical selected from the group consisting of halogen, alkyl of one to six carbon atoms, alkoxy of one to six carbon atoms, carboxyl derivatives, nitro, cyano, azido, ureido, ureylene, alkoxycarbonyloxy, hydroxyl, alkylamino, alkoxycarbonyl, trialkylsilyl, alkoxyimino, alkylsulfonyl, phenylsulfonyl and amino.

28. A pharmaceutical composition according to claim 27 wherein $R_2$ is pyridyl.

29. A pharmaceutical composition according to claim 28 wherein the compound is ethyl β-[[[[4-[4-(aminoiminomethyl)phenyl]butyl]amino]carbonyl]amino]-3-pyridinepropanoate.

30. A pharmaceutical composition according to claim 28 wherein the compound is β-[[[[4-[4-(aminoiminomethyl)phenyl]butyl]amino]carbonyl]amino]-3-pyridinepropanoic acid.

* * * * *

UNITED STATES PATENT AND TRADEMARK OFFICE
CERTIFICATE OF CORRECTION

PATENT NO. : 5,272,162      Page 1 of 5
DATED      : December 21, 1993
INVENTOR(S): Tjoeng, et al.

It is certified that error appears in the above-indentified patent and that said Letters Patent is hereby corrected as shown below:

Abstract, line 7, reading "compounds and" should read -- compounds, and --.

Column 3, line 35, reading "propanoat" should read -- propanoate --.

Column 4, line 5, reading "isoproylene" should read -- isopropylene --.

Column 4, line 11, reading "buenylene" should read -- butenylene --.

Column 4, line 18, reading "hexnylene" should read -- hexynylene --.

Column 4, line 41, reading "∫alkoxycarbonyl" refer" should read -- "alkoxycarbonyl" refers --.

Column 4, line 59, reading "refer to" should read -- refers to --.

Column 4, line 65, reading "66(I)," should read -- 66(1), --.

Column 5, line 59, reading "about I to" should read -- about 1 to --.

Column 9, line 50, in Method 2 reading "ClSO$_2$=C=O" should read -- ClSO$_2$N=C=O.

Column 10, line 18, should read --*Indicates Chiral Center--.

Column 10, line 43, should read --*Indicates Chiral Center--.

UNITED STATES PATENT AND TRADEMARK OFFICE
CERTIFICATE OF CORRECTION

PATENT NO. : 5,272,162
DATED : December 21, 1993
INVENTOR(S) : Tjoeng, et al.

It is certified that error appears in the above-indentified patent and that said Letters Patent is hereby corrected as shown below:

Column 10, line 62, the formula reading

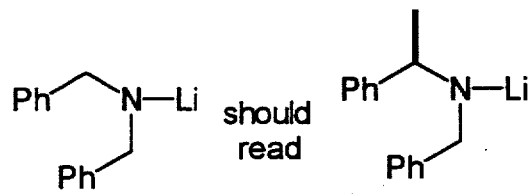

Column 11, line 7, the formula reading

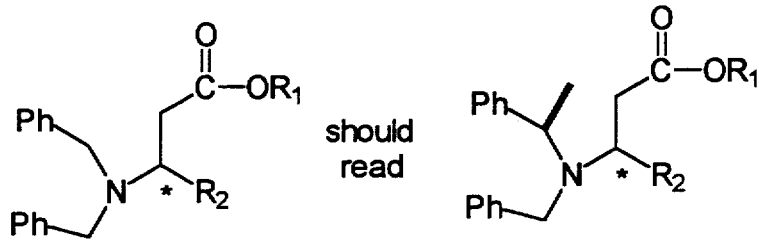

Column 13, line 28, reading "Anqew." should read --Angew.--.

Column 13, line 29, reading "Enol." should read --"Engl."--.

Column 13, line 43, reading "Method I)" should read --Method 1)--.

Column 13, line 54, reading "Oroanometallic" should read --Organometallic --.

UNITED STATES PATENT AND TRADEMARK OFFICE
CERTIFICATE OF CORRECTION

PATENT NO. : 5,272,162
DATED : December 21, 1993
INVENTOR(S) : Tjoeng, et al.

It is certified that error appears in the above-indentified patent and that said Letters Patent is hereby corrected as shown below:

Column 14, line 42, reading "which Will" should read -- which will --.

Column 14, line 57, reading "Anqew." should read --Angew.--.

Column 14, line 60, reading "shown Scheme" should read -- shown in Scheme --.

Column 15, line 15, reading "(19II)]." should read -- (1911)]. --.

Column 15, line 47, reading "18314-186" should read -- 183-186 --.

Column 16, line 57, reading "White solid" should read -- white solid --.

Column 17, line 26, reading "for I hour." should read -- for 1 hour. --.

Column 17, line 42, reading "CL:" should read -- Cl: --.

Column 17, line 63, reading "in vacuo. The" should read -- in vacuo, the --.

Column 17, line 67, reading "I.49 g" should read --1.49 g--.

Column 20, line 2, reading "EXAMPLE 4" should read -- EXAMPLE 4  Preparation of --.

Column 22, line 15, reading "1I mg/mL" should read -- 11 mg/mL --.

UNITED STATES PATENT AND TRADEMARK OFFICE
CERTIFICATE OF CORRECTION

PATENT NO. : 5,272,162  Page 4 of 5
DATED : December 21, 1993
INVENTOR(S) : Tjoeng, et al.

It is certified that error appears in the above-indentified patent and that said Letters Patent is hereby corrected as shown below:

Column 22, line 63, reading "(CD3OD)" should read --(CD$_3$OD)--.

Column 24, line 44, reading "b 2.42-2.51" should read -- 2.42-2.51 --.

Column 24, line 44, reading "CH$_2$NH)," should read --C$\underline{H}_2$NH),--.

Column 24, line 66, reading "2.50-2.57" should read -- 2.50-2.57 --.

Column 24, line 67, reading "5.05-5.16" should read -- 5.05-5.16 --.

Column 25, line 31, reading "-1-butyl" should read -- -1-butyl --.

Column 25, line 42, reading "-1-butyl" should read -- -1-butyl --.

Column 26, line 2, reading "2-3 x 10s" should read -- 2-3 x $10^8$ --.

Column 27, line 24, reading "ti six" should read --to six--.

Column 27, line 27, reading "optionally" should read --consisting --.

Column 27, line 28, reading "sic" should read -- six --.

Column 27, line 30, reading "axido," should read --azido,--.

Column 27, line 61, reading "sic" should read --six--.

UNITED STATES PATENT AND TRADEMARK OFFICE
CERTIFICATE OF CORRECTION

PATENT NO. : 5,272,162
DATED : December 21, 1993
INVENTOR(S) : Tjoeng, et al.

It is certified that error appears in the above-indentified patent and that said Letters Patent is hereby corrected as shown below:

Column 27, line 62, reading "A is" should read -- $R_1$ is --.

Column 28, line 48, reading "sic" should read --six--.

Column 28, line 63, reading "carbonyl" should read -- carboxyl --.

Column 28, line 64, reading "axido" should read --azido--.

Signed and Sealed this

Twenty-fifth Day of April, 1995

Attest:

BRUCE LEHMAN

Attesting Officer

Commissioner of Patents and Trademarks